United States Patent [19]
Grimm

[11] Patent Number: 5,938,583
[45] Date of Patent: Aug. 17, 1999

[54] PRECISION IMPLANT NEEDLE AND METHOD OF USING SAME IN SEED IMPLANT TREATMENT OF PROSTATE CANCER

[76] Inventor: Peter D. Grimm, 1211 E. Newton, Seattle, Wash. 98102

[21] Appl. No.: 08/999,404

[22] Filed: Dec. 29, 1997

[51] Int. Cl.$^6$ ............................. A61M 36/00; A61N 5/00
[52] U.S. Cl. ..................................................... 600/7; 600/1
[58] Field of Search .................................... 600/1–8, 564, 600/566; 604/51, 59, 60–64, 93, 164, 16–18

[56] References Cited

U.S. PATENT DOCUMENTS

| | | | |
|---|---|---|---|
| 4,086,914 | 5/1978 | Moore | 600/7 |
| 4,402,308 | 9/1983 | Scott | 600/7 |
| 4,697,575 | 10/1987 | Horowitz. | |
| 4,815,449 | 3/1989 | Horowitz. | |
| 5,242,373 | 9/1993 | Scott et al. | 600/7 |
| 5,626,829 | 5/1997 | Koutrouvelis. | |

OTHER PUBLICATIONS

Grimm, Blasko & Ragde, Ultrasound–Guided Transperineal Implantation of Iodine–125 and Palladium 103 for the Treatment of Eary Stage Prostate Cancer, *Atlas of the Urologic Clinics of North America*, vol. 2, No. 2, Oct. 1994.
Grimm, Glasko, Ragde, Sylvester & Clarke, Does Brachytherapy Have a Role in the Treatment of Prostate Cancer, *Hematology/Oncology Clincs of North America*, vol. 10, No. 3, Jun. 1996.

*Primary Examiner*—Samuel Gilbert
*Attorney, Agent, or Firm*—Jensen & Puntigam, P.S.

[57] ABSTRACT

The needle combination includes an insertion stylet which has a small diameter and is rigid. The tip of the insertion stylet is sharp for ease of insertion into the prostate. A needle sleeve has a larger diameter than the insertion stylet and is inserted into the prostate around the insertion stylet. A needle is loaded with radioactive seeds and spacers and is inserted, along with an implant stylet, into the sleeve after the insertion stylet has been removed. The needle and the sleeve are then removed together, while holding the implant stylet in place, so that the seeds are deposited in the prostate in desired locations.

11 Claims, 3 Drawing Sheets

PRECISION IMPLANT NEEDLE AND METHOD OF USING SAME IN SEED IMPLANT TREATMENT OF PROSTATE CANCER

TECHNICAL FIELD

This invention relates generally to radioactive seed implant treatment for prostate cancer and more specifically to a new needle combination for implanting such seeds into the prostate.

BACKGROUND OF THE INVENTION

Prostate cancer currently affects a significant number of men, particularly those in the age bracket of 50 to 80. In 1997 alone, 230,000 men will be diagnosed with prostate cancer. In the past, prostate cancer has often been diagnosed only when it was in an advanced and virtually incurable state. With the introduction of certain diagnostic measures, however, including the PSA blood test, as well as heightened public awareness, prostate cancer is now often being diagnosed at a relatively early and curable stage.

There are three fundamental treatments for prostate cancer, including radical prostatectomy (surgery), external beam radiation, and radioactive seed implantation. Radical prostatectomy has historically been very effective, but also has a relatively high rate of impotence, incontinence and surgical morbidity associated with it. External beam radiation has been reasonably effective for treatment of early stages of prostate cancer and has fewer side affects than radical prostatectomy. Beyond the early stages of the disease, however, external beam radiation decreases in effectiveness relative to the surgical procedure. The third technique, radioactive seed implantation, involves the placement of radioactive seed-like elements in the prostate gland. The radioactive seeds deliver high dosages of radiation to the prostate, but relatively low dosages to the surrounding tissue, such that the radiation is quite targeted to the prostate, resulting in the destruction of cancer cells in the prostate before they can spread to other parts of the body.

The original seed implantation procedure was an "open" implant technique. In this technique, the radioactive seeds were placed directly into the prostate gland through a surgical incision. However, this type of implant has proven to be relatively unsatisfactory, since the seeds are difficult to position properly.

A recent development involving radioactive seed implantation is referred to as transperineal seed implantation. This technique, which is described in more detail below, has had excellent results, generally equal to surgery (radical prostatectomy). Also known as brachytherapy, this technique is advantageous in that it can be performed on an outpatient basis, permitting the patient to resume normal activities in just a few days. The technique has proven to have relatively low incontinence and impotency rates and therefore has become increasingly attractive.

The goal of the transperineal technique is to significantly increase the accuracy of the placement of the radioactive seeds into predetermined locations within the prostate gland. This increase in accuracy is believed to account for the significant success rate of the technique and the other advantages discussed above. The transperineal technique uses a plurality of needles (typically 25–30 per treatement) to position the seeds within the prostate. The needles are used with a specialized stepper apparatus, an ultrasound probe and a template, for initially positioning, guiding and then moving the needles to proper placement within the prostate.

The needles currently used with the transperineal technique do have some disadvantages. The insertion of the needles can (and typically will) result in movement of the prostate. Because the seeds are designed to be placed in precise locations within the prostate, this movement of the prostate can result in seeds being slightly off the desired target area. Stabilizing needles have been used to attempt to minimize this disavantage, but they have not been completely successful and are expensive.

Further, the existing needles are loaded with the radioactive seeds prior to their insertion, along with spacer elements which separate adjacent seeds. Since the needles are metal, confirmation that the needle is correctly loaded is either not done or accomplished by radiographic examination, which can be time-consuming, somewhat difficult and is fairly expensive. It would be desirable to be able to verify the correct loading of the seeds more readily and quickly.

Still further, it is known that, in actual practice, five or more insertions per needle are typically necessary to position each needle correctly. This may result in significant trauma to the prostate, considering, as indicated above, that 25–30 needles are needed per treatment. Swelling of the prostate typically results, which also affects the accuracy of subsequently inserted needles. The accurate and proper placement of the needles is very important to the successful use of the seed implantation.

Significant experience in use of the technique is also important to its success. However, if one or more of the above-described disadvantages can be significantly reduced, then experience becomes somewhat less of a factor. This is important in the present situation, where the need for the technique is quite high and large numbers of physicians are undertaking initial training in the technique. The easier and more reliable the technique, the more quickly a physician can attain a high success rate.

SUMMARY OF THE INVENTION

Accordingly, the present invention is an article (and accompanying method), a needle combination, for use in radioactive seed implant treatment of prostate cancer, comprising: an insertion stylet which can be inserted into the prostate in a desired location; a sleeve element which has a larger diameter than the insertion stylet for insertion into the prostate over the insertion stylet; a needle in which radioactive seeds have been preloaded for implanting into the prostate, the needle being slightly smaller in diameter than the sleeve, so that when the insertion stylet is withdrawn from the sleeve, the needle can be inserted into the sleeve to a desired position therein; and an implant stylet configured and arranged for partial insertion into the needle and such that when the needle and the sleeve are withdrawn from the prostate along the implant stylet, the radioactive seeds are deposited in desired locations in the prostate.

BEST MODE FOR CARRYING OUT THE INVENTION

Figure 1:
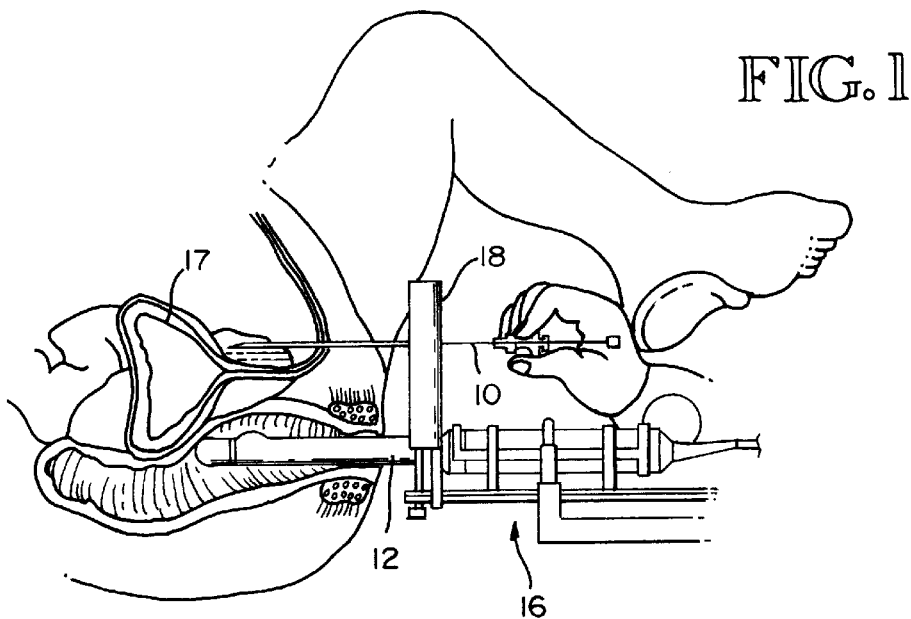
FIG. 1 is a diagram illustrating the general technique of transperineal seed implantation.

FIG. 1 illustrates the recent transperineal seed implantation technique. This technique is described in detail in an article entitled "Ultrasound Guided—Transperineal Implantation for the Treatment of Early Stage Prostate Cancer" by Grimm, Blasko and Ragde in the *Atlas of the Urologic Clinics of North America*, Volume II, Number 2, October 1994.

Generally, the patient is placed supine on an operating table and an ultrasound probe 12 is inserted into the patient's rectum. The ultrasound probe 12 is supported by a stabilizing and stepping unit shown generally at 16, which is secured to the operating table. The stepping unit 16 includes a template 18 which has a plurality of guide holes therein through which individual preloaded needles 10 are positioned. The preloaded ultrasound needles 10 are inserted through the template by the physician and then through the perineum area of the patient. The needles are inserted into the prostate 17 using ultrasound and accurately positioned therein, in accordance with a preplanned dosimetry pattern. The needles are inserted such that that the tip of each needle reaches a desired depth in the prostate. The template portion of the stepper apparatus, through which the needle is inserted, establishes the basic coordinates of each needle; each needle is inserted into a particular, predetermined location within the prostate.

Each preloaded needle has a predetermined number of seeds therein for the particular location where the needle is to be inserted into the prostate. The seeds in the needle are typically separated by spacers such that seeds and spacers alternate along a portion of the needle. A needle stylet is positioned partially within the needle, with the distal end of the stylet abutting the nearest seed in the needle. The needle is then withdrawn from the prostate, with the stylet being maintained in position by the operator. As the needle is slowly withdrawn, typically with small rotational movements by the operator, the line of successive seeds and spacers within the needle is disgorged from the needle and remains within the prostate along the line previously occupied by the withdrawing needle.

When all the needles, typically 25–30, which are to be used for the patient have been inserted and then withdrawn, leaving the radioactive seeds in place in the prostate, the ultrasound probe is withdrawn.

The above-described procedure using radioactive seeds (typically Iodine 125 or Palladium 103) is an outpatient procedure. Hence, the patient, after a short time in a recovery area, is typically discharged. The patient usually can resume normal activity within a few days.

This technique has tremendous advantages, particularly over surgical techniques, which require several months of recovery before even normal non-strenuous duties can be safely resumed.

The needle combination of the present invention shown in FIGS. 2 and 3 can be used with the stepping unit/template apparatus shown in FIG. 1. The first part of the needle combination is shown in FIG. 2a. It is a solid, small diameter (typically 19 gauge) surgical stainless steel insertion stylet 22. Typically, stylet 22 will be approximately 22 cm. long. Stylet 22 has a beveled tip portion 24, or alternatively a diamond tip, which in the embodiment shown has a sharp leading edge 25. The tip could also be a point. The stylet tip 24 is burnished to improve the ultrasound image, while the sharp leading edge is for ease of entry into and positioning in the prostate. The stylet 22, being solid, is relatively rigid, even though it has a small diameter, so that it can be more readily positioned within the prostate.

Figure 3A:
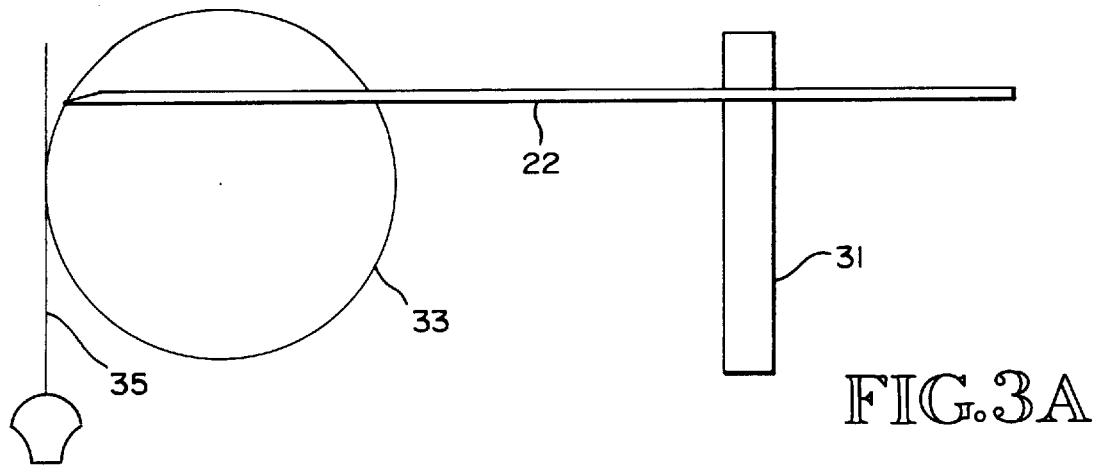
FIGS. 3a–3e show the sequential steps in the transperineal seed implantation technique using the needle combination of FIGS. 2a–2d.
Figure 3B:
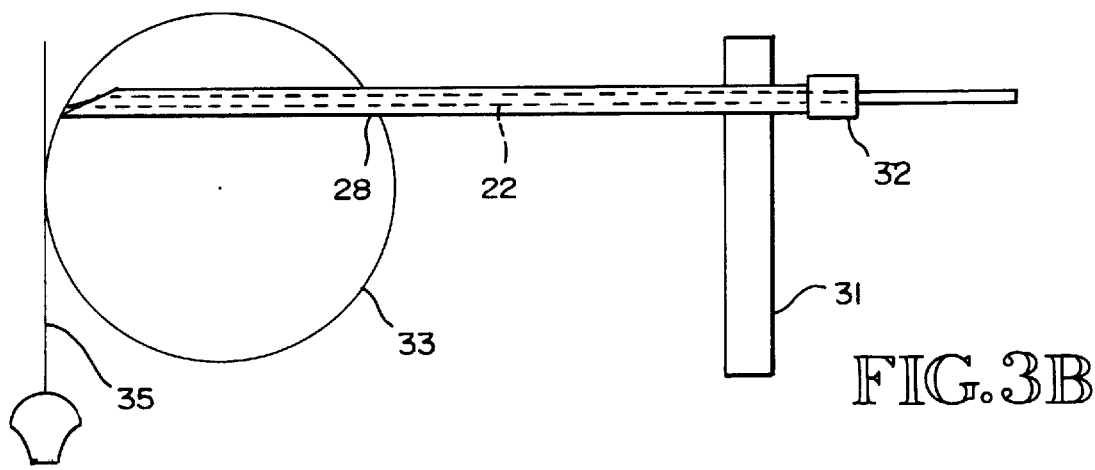

Following the successful insertion of the stylet, which is accomplished with the use of the ultrasound probe, as shown in FIG. 3a (which also shows the template 31, a representation of the prostate 33 and the ultrasound signal 35), a hollow sleeve 28 is inserted over the insertion stylet 22 into the prostate. A tip portion 30 of sleeve 28 also has a sharp leading edge 31, beveled like the insertion stylet of FIG. 2a. The internal diameter of the sleeve is large enough that it may be readily moved along the stylet 22. In the embodiment shown, sleeve 28 is 16 or 17 gauge stainless steel. At the other end of sleeve 18 is a hub portion 32. Hub portion 32 aids in the insertion of the sleeve by the physician. The insertion of sleeve 28, being made over the insertion stylet 22, which is already in place, will cause much less trauma to the prostate than with direct insertion of a loaded needle. This is illustrated in FIG. 3b.

Figure 2A:
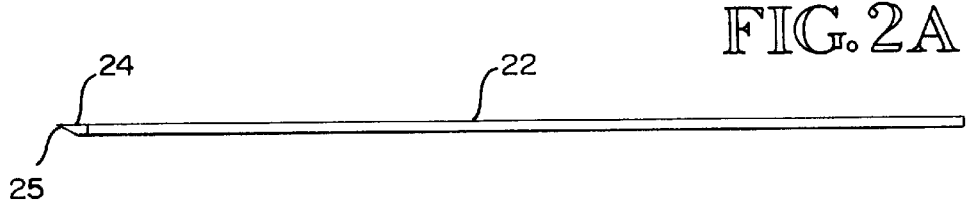
FIGS. 2a–2d illustrate the needle combination of the present invention for use in the technique shown in FIG. 1.
Figure 2B:
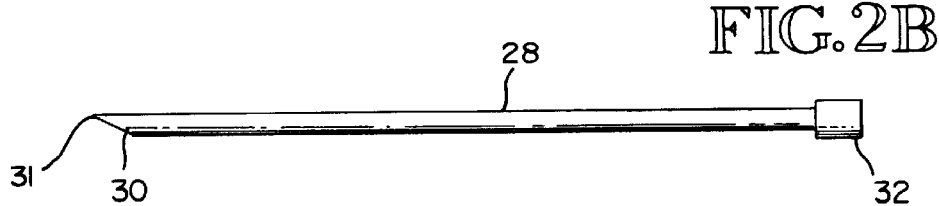
Figure 2C:
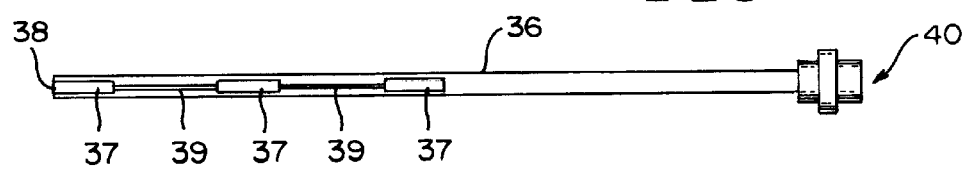
Figure 2D:
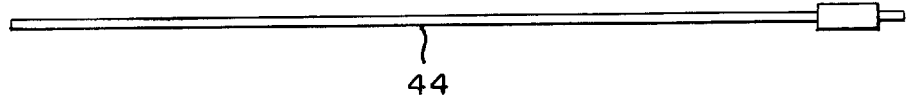

The needle portion 36 of the needle combination is shown in FIG. 2c. Needle 36 is loaded in the manner described above with successive radioactive seeds 37, alternating with spacer elements 39. The correct loading of the needle is easy to confirm, since the needle is made from surgical plastic material, which is transparent. Thus, a visual inspection is all that is necessary to confirm correct loading of the needle. This is advantageous over previous needles.

Figure 3C:
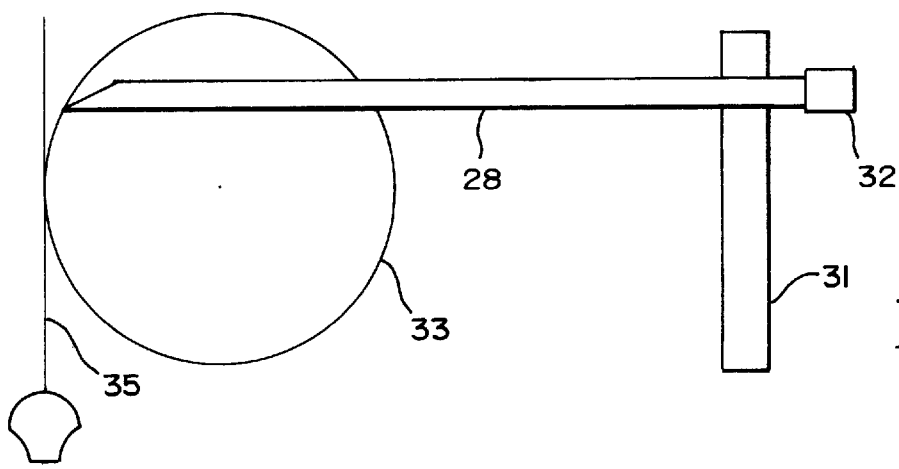
Figure 3D:
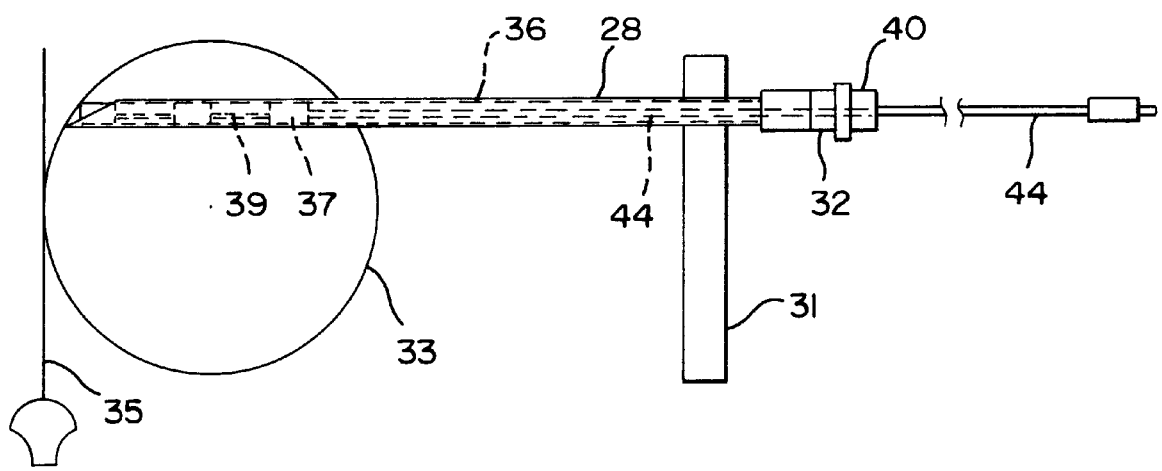

Insertion stylet 22 is withdrawn from sleeve 28, leaving just sleeve 28 in place, as shown in FIG. 3c. The loaded needle, which is approximately the same diameter as the insertion stylet 22, is then inserted into sleeve 28. Implant stylet 44 is also in place in the near end of the needle, abutting the nearest seed. Needle 36 has a square distal end 38, and the needle and stylet are inserted such that end 38 of the needle is coincident with the tip of sleeve 28. Needle 36 is now in proper position for placement of the seeds in the prostate. The ultrasound image produced by the probe (FIG. 1) is used to confirm the proper positioning of needle 36 within sleeve 28. Needle 36 has a hub element 40 at its rear end which is arranged to lock on to hub portion 32 of sleeve 28. The combination of sleeve 28 and needle 36, following locking of the two elements, is firmly and correctly positioned within the prostate. This is shown in FIG. 3a, along with the implant stylet 44.

Figure 3E:
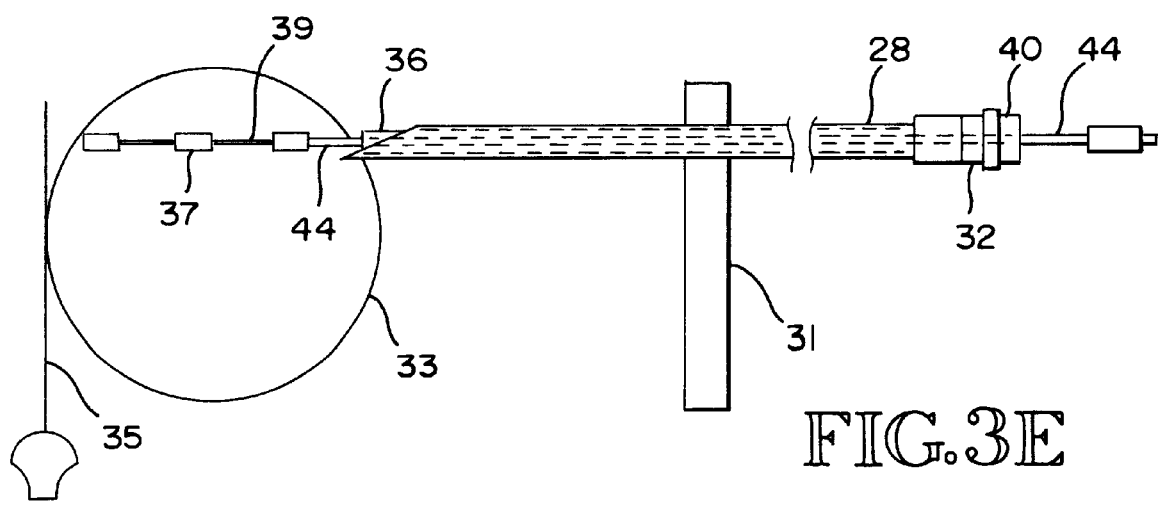

The needle 36 is now properly positioned with the prostate, with the blunt end 46 of stylet 44 in contact with the nearest spacer or seed element. At this point, implant stylet 44 is held in position by the operator while needle 36 and sleeve 28 together are slowly withdrawn, leaving a line of seeds and spacers along the line vacated by the withdrawing needle/sleeve. This is shown in FIG. 3e. The above process is repeated for successive needles until the prostate is completely implanted according to the preplanned dosimetry pattern.

The needle combination has several significant advantages over existing seed implant needles. First, the prostate is better stabilized by the use of the insertion stylets. The insertion stylet, having a sharp point and being rigid and smaller than the sleeve, means less trauma and swelling of the prostate. When the sleeve is then inserted over the stylet, and then the insertion stylet removed, the preloaded needle can be easily inserted into the sleeve and properly located, without any need for repeated insertions. If the needle is inserted too deeply, e.g. into the bladder, that will be immediately recognized by the operator because of the presence of urine in the needle. This arrangement also prevents prostate tissue from jamming the end of the needle, so as to prevent improper placement of the seeds in the prostate. The need for stabilizing needles is eliminated, and the proper loading of seeds within the needle can be quickly determined by visual inspection.

The resulting simplicity of the seed implantation technique using the new needle combination will reduce multiple insertions and permit less experienced practitioners to be successful without as much instruction and experience as heretofore.

Although a preferred embodiment of the invention has been disclosed for illustration, it should be understood that various changes, modifications and substitutions may be incorporated in such embodiment without departing from the spirit of the invention which is defined by the claims which follow.

What is claimed is:

1. A needle kit for use in radioactive seed implant treatment of prostate cancer, comprising:

an insertion stylet adapted for insertion into the prostate in a desired location;

a needle sleeve having a larger diameter than the insertion stylet, the needle sleeve adapted for insertion into the prostate over the insertion stylet;

a needle in which radioactive seeds are loaded for implanting into the prostate, the needle being slightly smaller in diameter than the sleeve, so that when the insertion stylet is withdrawn from the sleeve, the needle can be inserted into the sleeve to a desired position therein;

an implant stylet configured and arranged for partial insertion into the needle and such that when said needle and said sleeve are withdrawn from the prostate along the implant stylet, the radiactive seeds are deposited in desired locations in the prostate.

2. A needle kit of claim 1, wherein the needle comprises transparent material so that proper loading of the seeds therein can be readily visually confirmed.

3. A needle kit of claim 1, wherein the insertion stylet is rigid and has a smaller diameter than the needle, permitting convenient and accurate insertion of the insertion stylet into the prostate.

4. A needle kit of claim 1, wherein a near end of the sleeve has a hub portion thereon and the needle has a mating end portion for locking onto said hub portion of the sleeve, resulting in the sleeve and the needle being readily movable together.

5. A needle kit of claim 1, wherein the insertion stylet and the sleeve both have distal end portions which are sharpened, for ease of insertion into the prostate.

6. A needle kit of claim 1, wherein the implant needle and the implant stylet both have distal ends which are blunt.

7. A method of treatment of prostate cancer using radioactive seeds, comprising the steps of:

inserting an insertion stylet into the prostate to a desired location;

inserting a sleeve having a larger diameter than the insertion stylet into the prostate over the insertion stylet;

removing the insertion stylet from the sleeve;

inserting a needle preloaded with radioactive seeds with a partially inserted implant stylet into the sleeve to a desired location within the prostate;

maintaining the implant stylet in position while withdrawing the needle and the sleeve, leaving the seeds previously in the needle in place in the prostate and removing any portions of the needle, sleeve and implant stylet still remaining in the prostate therefrom.

8. A method of claim 7, wherein the insertion stylet is rigid and has a diameter which is smaller than the needle.

9. A method of claim 7, wherein the needle is transparent, permitting visual inspection of the loaded seeds in the needle.

10. A method of claim 7, including the step of securing the needle to the sleeve upon insertion of the needle, so that the needle and the sleeve can be withdrawn together from the prostate along the implant stylet.

11. A method of claim 7, wherein the insertion stylet and the sleeve both have distal ends which are sharpened and the needle and the implant stylet both have distal ends which are blunt.

* * * * *